United States Patent [19]

Sturm

[11] 4,203,978
[45] May 20, 1980

[54] AMIDINO-PHOSPHORIC ACID THIOL ESTERS FOR COMBATING PESTS

[75] Inventor: Elmar Sturm, Aesch, Switzerland

[73] Assignee: Ciba-Geigy Corporation, Ardsley, N.Y.

[21] Appl. No.: 919,335

[22] Filed: Jun. 26, 1978

Related U.S. Application Data

[63] Continuation-in-part of Ser. No. 862,695, Dec. 21, 1977, abandoned.

[30] Foreign Application Priority Data

Dec. 30, 1976 [CH] Switzerland .................. 16473/76
Mar. 4, 1977 [CH] Switzerland .................... 2721/77

[51] Int. Cl.² .......................... A01N 9/36; C07F 9/24
[52] U.S. Cl. ..................................... 424/211; 260/944
[58] Field of Search ......................... 260/944; 424/211

[56] References Cited

U.S. PATENT DOCUMENTS 3,925,517  12/1975  Pissiotas et al. .................. 260/944

Primary Examiner—Anton H. Sutto
Attorney, Agent, or Firm—Harry Falber

[57] ABSTRACT

Amidino-phosphoric acid thiol esters hereinafter defined in formula I are useful as active ingredients in pesticidal compositions containing them. They are useful for combating insects, Acarina, ectoparasites and particularly nematodes.

20 Claims, No Drawings

AMIDINO-PHOSPHORIC ACID THIOL ESTERS FOR COMBATING PESTS

CROSS-REFERENCE

This application is a continuation-in-part application of application Ser. No. 862,695, filed Dec. 21, 1977, now abandoned.

The present invention relates to amidino-phosphoric acid thiol esters, to a process for producing them, to pesticidal compositions containing these compounds as active ingredients, and to the use of the novel compounds for combating insects, Acarina and particularly nematodes.

The novel amidino-phosphoric acid thiol esters constitute a closely limited group of highly effective compounds and they correspond to the formula I

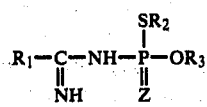

wherein
R₁ represents hydrogen, $C_1$–$C_4$-alkyl or cyclopropyl,
R₂ represents $C_3$–$C_5$-alkyl, and
R₃ represents methyl or ethyl, whilst
Z represents oxygen or sulphur.

An important subgroup of compounds are those of the formula I wherein Z represents oxygen. Within this group preferred compounds are those wherein
R₁ represents methyl, ethyl or cyclopropyl,
R₂ represents n-propyl or sec. butyl and
R₃ represents ethyl.

Another important subgroup of compounds of the formula I is formed by those in which Z represents sulphur and R₃ represents ethyl. Within this group preferred compounds are those wherein R₁ represents methyl or cyclopropyl and R₂ represents n-propyl or sec. butyl.

By the alkyl groups given are meant, dependent on the definition given for R₁ and R₂, methyl, ethyl, propyl, isopropyl as well as the isomeric butyl and amyl groups. Phosphorylated formamidines have already become known from the German Offenlegungsschriften Nos. 2,312,738 and 2,451,911. Their nematocidal action is however very unsatisfactory. Furthermore, they do not have the high level of soil stability which is essential for combating soil pests.

It has now been shown that the compounds of the formula I of the present invention satisfy to a high degree both of the requirements mentioned above. This is particularly surprising because compounds which are directly homologous have these properties in only a slightly pronounced form, so that for practical purposes they are unsuitable.

The process disclosed and exemplified in USP. 3,734,980, col. 2, lines 20 to 54, which comprises reacting O,O-dialkyl thionophosphoryl amidines and alkyl iodide to yield O,S-mixed esters of phosphoryl amidines results in clearly defined end products only if the alkyl moieties on the phosphorous atom are all the same. With different alkyl groups the lowest alkyl moiety tends to migrate to the sulfur atom. Not surprisingly therefore the O,S-mixed ester type in this reference is exemplified by O,S-dimethylphosphorylamidines only. The disclosed process when carried out with two or three different alkyl groups present results in a mixture of various endproducts. This is caused by competing migration of all alkyl moieties at the phosphorus atom whereby the alkylthio group contains predominantly the alkyl group of lowest molecular weight.

It is clear, therefore, that compounds of the formula I of this invention having Z=oxygen cannot be obtained following the above process. The compounds of this invention are new.

They are obtained according to another aspect of the invention by one of the following processes 1 and 2:

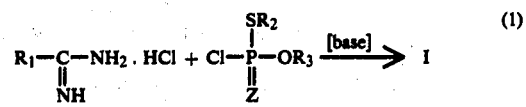

whereby Z, R₁, R₂ and R₃ have the meanings given for the formula I, and the HCl salt of the amidine is representative of possible other salts of customary acids (hydrohalic acids, sulphuric acid, phosphoric acid, etc.); its presence is however not essential with regard to the course of the reaction.

If Z represents oxygen, compounds of the formula I can especially be produced as follows

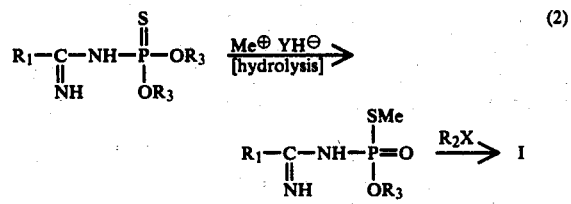

whereby X represents halogen, preferably chlorine, bromine or iodine, or alternatively a sulphate radical, Me represents alkali metal, alkaline-earth metal or NH₄, and Y represents oxygen or sulphur.

In process (1) involving amidation of a thiophosphoric acid ester chloride, reaction temperatures of 0° to 100° C., preferably 10°–45° C., are applied.

The reaction (1) is performed in solvents or diluents which are inert to the reactants. The following are for example suitable: aliphatic or aromatic hydrocarbons such as benzene, toluene, xylenes or petroleum ether; halogenated hydrocarbons such as chlorobenzene, methylene chloride, ethylene chloride or chloroform; ethers and ethereal compounds such as dialkyl ethers, dioxane or tetrahydrofuran; nitriles such as acetonitrile; N,N-dialkylated amides such as dimethylformamide; water; or ketones such as methyl ethyl ketone, dimethylsulphoxide, and mixtures of such solvent with each other. Two-phase reaction mediums, e.g. methylene chloride/water, are particularly preferred. The reaction proceeds in the presence of an acid-binding agent or condensation agent. The following are suitable:tertiary amines such as trialkylamines (e.g. triethylamine), pyridine and pyridine bases, or inorganic bases, such as the oxides and hydroxides, hydrogen carbonates and carbonates of alkali metals and alkaline-earth metals as well as sodium acetate (see German Offenlegungsschrift No. 2,451,911).

Process (2) involving transesterification of an amidinophosphoric acid thiono ester is performed in the temperature range of 20°–100° C. The hydrolysis step is performed in the presence of the above defined hydroxide or hydrogen sulphide MeYH. Also suitable however as the reaction medium are mixtures of water and an immiscible solvent, such as a hydrocarbon (e.g. benzene) or chlorinated hydrocarbon (e.g. chloroform), in the sense of a phase-transfer method. In this case, the simultaneous use of quaternary ammonium salts, such as tetrabutylammonium bromide, is advantageous.

In the second reaction stage, entailing alkylation of the formed thiol salt, nonaqueous polar solvent, e.g. acetonitrile or dimethylformamide, are used (see U.S. Pat. No. 3,896,193).

The two aforementioned reaction courses (1) and (2) are, for the $R_2S$-/$R_3O$-alkyl-unsymmetrically substituted compounds of the formula I, practicable ways of obtaining pure end products.

Compounds of the formula I are stable under neutral conditions, and have in the soil a prolonged action against nematodes. This is very surprising since compounds of the formula II are ineffective against nematodes:

$$R_1-\underset{\underset{NH}{\|}}{C}-NH-\underset{\underset{OR_3}{|}}{\overset{\overset{S}{\|}}{P}}-OR_3 \quad (II)$$

($R_1$ herein has the meaning given under the formula I, and $R_3$ represents methyl or ethyl).

The following Examples illustrate the production of the active substances according to the invention. The temperature values are given in degrees Centigrade.

EXAMPLE 1

20 g (0.21 mole) of acetamidine hydrochloride is dissolved in 100 ml of water. A solution of 40 g (0.2 mole) of O-ethyl-S-n-propylthiophosphoric acid chloride in 400 ml of methylene chloride is added portionwise with vigorous stirring. To the reaction mixture is then added dropwise an 0.4 molar NaOH solution, which corresponds to 16 g of solid NaOH. The temperature meanwhile rises to about 30°. After completion of the reaction, stirring is maintained for about 4 hours at room temperature; the methylene chloride layer is separated, dried over sodium sulphate and concentrated by evaporation to yield 38 g of N-(O-ethyl-S-n-propylthiophosphoryl)-acetamidine as viscous oil, which solidifies after a short time into the form of colourless crystals, m.p. 48°–50° [Compound No. 2].

EXAMPLE 2

(a) Production of the intermediate 20 g (0.21 mole) of acetamidine hydrochloride is dissolved in 100 ml of water. This solution is underlayed with 300 ml of methylene chloride, and 38 g (0.2 mole) of O,O-diethylthiophosphoric acid chloride is added. To the stirred reaction mixture is added dropwise a solution of 16 g (0.4 mole) of NaOH in about 200 ml of water. The phases are separated after four hours' stirring at room temperature. The dried methylene chloride phase yields, after concentration in vacuo, 40 g of N-(O,O-diethyl-thiophosphoryl)-acetamidine as viscous oil, which slowly solidifies to form colourless crystals, m.p. 34°–35°.

(b) Partial hydrolysis and S-alkylation 21 g (0.1 mole) of the intermediate obtained under (a) with 6 g (0.12 mole) of NaHS in 200 ml of methylcellosolve is heated at 100° for 5 hours; 15 g of n-propyl bromide is added to the cloudy solution, and stirring is maintained at 80° for 2 hours. The reaction mixture is concentrated in vacuo to dryness. The oily/crystalline residue is shaken with water and methylene chloride, and the organic phase is concentrated to dryness to yield 18 g of a crystalline mass, which is recrystallised from ether/petroleum ether. The resulting pure N-(O-ethyl-S-n-propylthiophosphoryl)-acetamidine melts at 55°–57° [Compound No. 2].

EXAMPLE 3

A two phase mixture of 12 g cyclopropane carbamidine hydrochloride of the formula

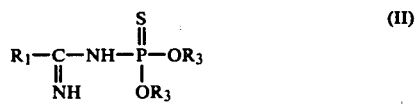

in 20 ml of water and 21.7 g O-ethyl-S-sec. butyl chlorophosphorothioate in 150 ml of dichloromethane was stirred vigorously. There was added dropwise an aqueous solution of 8 g sodium hydroxide at 10°–20° C. After completed addition the mixture was stirred for 4 hours at ambient temperature, the phases were separated, the methylene chloride layer washed, dried and evaporated, 22 g of O-Ethyl-S- sec. -butyl-cyclopropanecarbamidino-thiophosphate were obtained as colorless viscous oil, $n_D^{20}=1.5135$ [Compound No. 12].

According to Examples 1, 2 or 3 or to any of the abovementioned methods the following compounds may be prepared:

| | | |
|---|---|---|
| (1) | H—C(=NH)—NH—P(=O)(OC$_2$H$_5$)(SC$_3$H$_7$(n)) | $n_D^{20} = 1.5210$ |
| (2) | CH$_3$—C(=NH)—NH—P(=O)(OC$_2$H$_5$)(SC$_3$H$_7$(n)) | m.p. 55°–57° |
| (3) | isoC$_3$H$_7$—C(=NH)—NH—P(=O)(OC$_2$H$_5$)(SC$_3$H$_7$(n)) | $n_D^{20} = 1.4986$ |
| (4) | CH$_3$—C(=NH)—NH—P(=O)(OC$_2$H$_5$)(SC$_4$H$_9$(n)) | $n_D^{20} = 1.5120$ |
| (5) | CH$_3$—C(=NH)—NH—P(=O)(OC$_2$H$_5$)(S—CH(CH$_3$)$_2$) | m.p. 83°–88° |
| (6) | H—C(=NH)—NH—P(=O)(OC$_2$H$_5$)(S—C$_5$H$_{11}$(n)) | $n_D^{20} = 1.5071$ |
| (7) | H—C(=NH)—NH—P(=O)(OC$_2$H$_5$)(S—CH(CH$_3$)—CH$_2$—CH$_3$) | $n_D^{20}$ 1.5104 |
| (8) | CH$_3$—C(=NH)—NH—P(=O)(OC$_2$H$_5$)(S—CH$_2$—CH(CH$_3$)—CH$_3$) | m.p. 75°–78° |

-continued

| (9) | isoC₃H₇–C(=NH)–NH–P(=O)(OC₂H₅)(S–CH₂–CH(CH₃)–CH₃) | $n_D^{20}$ = 1.4625 |
|---|---|---|
| (10) | nC₄H₉–C(=NH)–NH–P(=O)(OC₂H₅)(S–C₃H₇(n)) | $n_D^{20}$ = 1.4951 |
| (11) | cyclopropyl–C(=NH)–NH–P(=O)(OC₂H₅)(S–C₃H₇(n)) | $n_D^{20}$ = 1.5073 |
| (12) | cyclopropyl–C(=NH)–NH–P(=O)(OC₂H₅)(S–CH(CH₃)–CH₂–CH₃) | $n_D^{20}$ = 1.5135 |
| (13) | CH₃–C(=NH)–NH–P(=O)(OC₂H₅)(S–C₄H₉(sek.)) | m.p. 78°–81° |
| (14) | CH₃–CH(CH₃)–C(=NH)–NH–P(=O)(OC₂H₅)(S–C₄H₉(sek.)) | $n_D^{20}$ = 1.4952 |
| (15) | H–C(=NH)–NH–P(=O)(OC₂H₅)(SCH₂–CH(CH₃)₂) | $n_D^{20}$ 1.5091 |
| (16) | C₂H₅–C(=NH)–NH–P(=O)(OC₂H₅)(SC₃H₇) | $n_D^{20}$ 1.5069 |
| (17) | C₂H₅–C(=NH)–NH–P(=O)(OC₂H₅)(S–CH₂–CH(CH₃)₂) | $n_D^{20}$ 1.4978 |
| (18) | n-C₃H₇–C(=NH)–NH–P(=O)(OC₂H₅)(SC₃H₇) | $n_D^{20}$ 1.5035 |
| (19) | H–C(=NH)–NH–P(=S)(OC₂H₅)(SC₃H₇(n)) | m.p. 53°–57° |
| (20) | CH₃–C(=NH)–NH–P(=S)(OC₂H₅)(SC₃H₇(n)) | m.p. 76°–78° |
| (21) | C₂H₅–C(=NH)–NH–P(=S)(OC₂H₅)(SC₃H₇(n)) | $n_D^{20}$ = 1.5529 |
| (22) | (n)C₃H₇–C(=NH)–NH–P(=S)(OC₂H₅)(SC₃H₇(n)) | $n_D^{20}$ = 1.5445 |
| (23) | (n)C₄H₉–C(=NH)–NH–P(=S)(OC₂H₅)(SC₃H₇(n)) | $n_D^{20}$ = 1.5369 |
| (24) | (CH₃)₂CH–CH₂–C(=NH)–NH–P(=S)(OC₂H₅)(SC₃H₇(n)) | oil |
| (25) | cyclopropyl–C(=NH)–NH–P(=S)(OC₂H₅)(SC₃H₇(n)) | $n_D^{20}$ = 1.5659 |
| (26) | isoC₃H₇–C(=NH)–NH–P(=S)(OC₂H₅)(SC₃H₇(n)) | $n_D^{20}$ = 1.5406 |
| (27) | CH₃–C(=NH)–NH–P(=S)(OC₂H₅)(S–CH(CH₃)–CH₂–CH₃) | viscous oil |
| (28) | CH₃–C(=NH)–NH–P(=S)(OC₂H₅)(S–CH₂–CH(CH₃)₂) | viscous oil |
| (29) | isoC₃H₇–C(=NH)–NH–P(=S)(OC₂H₅)(S–CH(CH₃)–CH₂CH₃) | viscous |
| (30) | isoC₃H₇–C(=NH)–NH–P(=S)(OC₂H₅)(S–CH₂–CH(CH₃)₂) | viscous |

EXAMPLE 4

20 g (0.21 mole) of acetamidine hydrochloride is dissolved in 100 ml of water. A solution of 44 g (0.2 mole) of O-ethyl-S-n-propyl-thionothiol-phosphoric acid chloride in 400 ml of methylene chloride is added portionwise with vigorous stirring. To the reaction mixture is then added dropwise an 0.4 molar NaOH solution, which corresponds to 16 g of solid NaOH. The temperature rises meanwhile to about 30°. After completion of the reaction, stirring is maintained for about 4 hours at room temperature; the methylene chloride layer is separated, dried over sodium sulphate and concentrated by evaporation to yield 40 g of N-(O-ethyl-S-n-propyl-thiono-thiolphosphoryl)-acetamidine in the form of colourless crystals, m.p. 76°–78° [Compound No. 20].

Also the following compounds are obtained after the manner of Example 4:

Compounds of the formula I are effective in particular against nematodes of the phytopathogenic type; among these are to be mentioned the following genera: Meloidogyne, Radopholus, Pratylenchus, Ditylenchus, Heterodera, Paratylenchus, Belonolaismus, Trichodorus and Longidorus. The special advantage of these compounds is their systemic action, which enables the pests to be combated not only be means of soil treatment but also by means of leaf application through the plant to be protected (basipetal transport).

Advantageous compositions are those which enable a uniform distribution of the active substance throughout a layer of soil extending to a depth of 10 to 20 cm to be ensured. The manner and form of application are dependent in particular on the type of plant, on the climate and on the conditions of the soil. Since the novel active substances are as a rule not phytotoxic and do not impair the capability of germinating, they can be applied usually, without observance of a "waiting period", immediately before or after the sowing of the plants. It is likewise possible to treat already existing crops of plants with the novel compositions. In addition, for the purpose of effecting an increase, specific parts of plants, such as seeds, sections of stalk (sugar-cane) or bulbs, as well as roots or seedlings, can be dressed with dispersions or solutions of the active substances.

Besides having an excellent nematocidal action, the compounds of the formula I have a distinct insecticidal, acaricidal, ectoparasitic and, in some cases, also fungicidal and bactericidal action.

The compounds of the formula I can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers. For widening their sphere of action, the compounds of the formula I can be combined with known insecticides, acaricides or nematocides, as well as with fungicides, herbicides, molluscicides or rodenticides.

The content of active substance in commercial compositions is between 0.1 and 90%.

For application, the compounds of the formula I can be in the following forms (the weight-percentage figures in brackets signify advantageous amounts of active substance):

solid preparations:
  dusts and scattering agents (up to 10%), granulates [coated granules, impregnated granules and homogeneous granules] (1 to 80%);

liquid preparations:
  (a) water-dispersible concentrates of active substance: wettable powders and pastes (25 to 90% in the commercial packing, 0.01 to 15% in ready-for-use solutions); emulsion concentrates and solution concentrates 10 to 50%, 0.01 to 15% in ready-for-use solutions);
  (b) solutions (0.1 to 20%).

The active substances of the formula I of the present invention can be formulated for example as follows:

Dust:
  The following substances are used to produce (a) a 5% dust and (b) a 2% dust:
  (a)
    5 parts of active substance, and
    95 parts of talcum;
  (b)
    2 parts of active substance,
    1 part of highly dispersed silicic acid, and
    97 parts of talcum.

The active substances are mixed and ground with the carriers, and in this form they can be applied by dusting.

Granulate:
  The following substance are used to produce a 5% granulate:
    5 parts of active substance,
    0.25 part of epichlorohydrin,
    0.25 part of cetyl polyglycol ether,
    3.50 parts of polyethylene glycol, and
    91 parts of kaolin (particle size 0.3-0.8 mm).

The active substance is mixed with the epichlorohydrin and dissolved in 6 parts of acetone; the polyethylene glycol and cetyl polyglycol ether are then added. The solution thus obtained is sprayed onto kaolin, and the acetone is subsequently evaporated off in vacuo. A microgranulate of this kind is advantageously used for combating soil pests.

Wettable powder:
  The following constituents are used to produce (a) a 70% wettable powder, (b) a 40% wettable powder, (c) and (d) a 25% wettable powder, and (e) a 10% wettable powder:
  (a)
    70 parts of active substance,
    5 parts of sodium dibutylnaphthylsulphonate,
    3 parts of naphthalenesulphonic acid/phenolsulphonic acid/formaldehyde condensate 3:2:1,
    10 parts of kaolin, and
    12 parts of Champagne chalk;
  (b)
    40 parts of active substance,
    5 parts of sodium lignin sulphonate,
    1 part of sodium dibutylnaphthalenesulphonate, and
    54 parts of silicic acid;
  (c)
    parts of active substance,
    4.5 parts of calcium lignin sulphonate,
    1.9 parts of Champagne chalk/hydroxyethylcellulose mixture (1:1),
    1.5 parts of sodium dibutylnaphthalenesulphonate,
    19.5 parts of silicic acid,
    19.5 parts of Champagne chalk, and
    28.1 parts of kaolin;
  (d)
    25 parts of active substance,
    2.5 parts of isooctylphenoxy-polyoxyethylene-ethanol,
    1.7 parts of Champagne chalk/hydroxyethylcellulose mixture (1:1),
    8.3 parts of sodium aluminum silicate,
    16.5 parts of kieselguhr, and
    46 parts of kaolin; and
  (e)
    10 parts of active substance,
    3 parts of a mixture of the sodium salts of saturated fatty alcohol sulphates,
    5 parts of naphthalenesulphonic acid/formaldehyde condensate, and
    82 parts of kaolin.

The active substances are intimately mixed in suitable mixers with the additives, and the mixture is then ground in the appropriate mills and rollers. There are obtained wettable powders which have excellent wetting and suspension properties and which can be diluted with water to give suspensions of the desired concentration. These can be used in particular for soil and leaf application.

Emulsifiable concentrate:
  The following substances are used to produce a 25% emulsifiable concentrate:
    25 parts of active substance,
    2.5 parts of epoxidised vegetable oil,
    10 parts of an alkylarylsulphonate/fatty alcohol polyglycol ether mixture,
    5 parts of dimethylformamide, and
    57.5 parts of xylene.

Emulsions of the desired concentration can be prepared from these concentrates by dilution with water.

EXAMPLE 5

Test To Determine The Nematocidal Action

In order to test its action against soil nematodes, the active substance is added, at a concentration of 10 and 2.5 ppm, to soil and sand, respectively, infested with root-gall nematodes (Meloidogyne incognita), and thoroughly mixed in. In the soils prepared in this manner, there are planted immediately afterwards on the one hand tomato seedlings and on the other hand tobacco seedlings. An assessment of the nematocidal action is made, 28 days after planting, by counting the galls present on the roots.

Compounds of the formula I showed in the above test a good action against Meloidogyne incognita, as can be seen from the mean values of three parallel tests. The assessment was based on the following scale of ratings:
0=0–5% infestation
1=5–25% infestation
2=25–80% infestation
3=above 80% infestation (ineffective).

The compounds of the formula I exhibited at an activesubstance concentration of 10 ppm without exception a complete action (rating 0); at 2.5 ppm they exhibited an almost complete action with a reduction of infestation to 0 to 25% (rating 0 or 1). The compounds Nos. 2, 11, 12, 13, 14, 16, 20, 23, 25, 26 and 27 proved also at this concentration to be fully effective (rating 0).

Compounds which structurally are directly homologous, such as

A  $CH_3-\underset{\underset{NH}{\|}}{C}-NH-\underset{\underset{O}{\|}}{\overset{\overset{SCH_3}{|}}{P}}-OCH_3$  m.p. 130°–135° C. (known from USP. 3,734,980 col. 1, line 61)

B  $CH_3-\underset{\underset{NH}{\|}}{C}-NH-\underset{\underset{O}{\|}}{\overset{\overset{SC_2H_5}{|}}{P}}-OC_2H_5$  semicrystalline C  $CH_3-\underset{\underset{NH}{\|}}{C}-NH-\underset{\underset{S}{\|}}{\overset{\overset{OC_2H_5}{|}}{P}}-OC_2H_5$  m.p. 34°–35° exhibited, even with high dosages of 25 ppm and 50 ppm, no nematocidal action whatsoever.

EXAMPLE 6

Insecticidal Action: *Dysdercus fasciatus*

Cotton plants were sprayed with an aqueous emulsion containing 0.05% of the compound to be tested (obtained from a 10% emulsifiable concentrate). After the coating had dried, the plants were infested with larvae of the species Dysdercus fasciatus in the $L_3$-stage. Two plants were used for each test compound, and the destruction rate attained was determined after 2, 4, 8, 24 and 48 hours. The test was carried out at 24° C. with 60% relative humidity. The compounds Nos. 2, 8, 16 and 20 effected after 8 hours a complete destruction of the larvae.

EXAMPLE 7

Systemic-insecticidal action: Aphis fabae

In order to determine the systemic action, rooted bean plants (Vicia faba) were placed into a 0.01;L % aqueous solution of the active substance (obtained from a 10% emulsifiable concentrate). After 24 hours, bean aphids (Aphis fabae) were placed onto the parts of the plants that had been above the soil. By means of a special device, the bean aphids were protected from the effects of contact and gas. The test was carried out at 24° C. with 70% relative humidity.

The compounds Nos. 2, 3 and 8, transported in the sap stream of the plant, effected a complete destruction of the bean aphids.

EXAMPLE 8

Acaricidal action

Bean plants (Phaseolus vulgaris) were infested, 12 hours before the test, with an infested piece of leaf from a mass culture of Tetranychus urticae. The transferred mobile stages were sprayed with the emulsified test preparations from a chromatography-sprayer in a manner ensuring no overflow of the spray liquor. An assessment was made after 2 to 7 days at 25° C. in a greenhouse, by examination under a binocular microscope, of the living and of the dead larvae, adults and eggs. The compounds of the formula I effected, at the latest after 7 days, a complete destruction both of the larvae and of the adult Acarina species.

I claim:

1. A compound of the formula I $$R_1-\underset{\underset{NH}{\|}}{C}-NH-\underset{\underset{Z}{\|}}{\overset{\overset{SR_2}{|}}{P}}-OR_3 \quad (I)$$

wherein
$R_1$ represents hydrogen, $C_1$-$C_4$-alkyl or cyclopropyl,
$R_2$ represents $C_3$-$C_5$-alkyl, and
$R_3$ represents methyl or ethyl, whilst
Z represents oxygen or sulphur.

2. A compound according to claim 1, wherein Z represents oxygen.

3. A compound according to claim 2, wherein
$R_1$ represents methyl, ethyl or cyclopropyl,
$R_2$ represents n-propyl or sec. butyl and
$R_3$ represents ethyl.

4. A compound according to claim 1, wherein Z represents sulphur and $R_3$ represents ethyl.

5. A compound according to claim 4, wherein
$R_1$ represents methyl or cyclopropyl and
$R_2$ represents n-propyl or sec. butyl.

6. N-(O-Ethyl-S-n-propyl-thiono-thiol-phosphoryl)-isobutyramidine of the formula $$CH_3-\underset{CH_3}{\overset{|}{CH}}-\underset{\underset{NH}{\|}}{C}-NH-\underset{\underset{S}{\|}}{\overset{\overset{S-CH_2CH_2CH_3}{|}}{P}}-OC_2H_5$$

according to claim 1.

7. N-(O-Ethyl-S-n-propyl-thiono-thiol-phosphoryl)-acetamidine according to claim 1.

8. N-(O-Ethyl-S-n-propyl-thiophosphoryl)-acetamidine according to claim 1.

9. O-Ethyl-S-sec.butyl-cyclopropanecarbamidino-thiophosphate according to claim 1.

10. A pesticidal composition comprising as active ingredient an effective amount of a compound according to claim 1, together with a suitable carrier.

11. A composition according to claim 10, wherein the active ingredient is a compound according to claim 2.

12. A composition according to claim 10, wherein the active ingredient is a compound according to claim 3.

13. A composition according to claim 10, wherein the active ingredient is a compound according to claim 4.

14. A composition according to claim 10, wherein the active ingredient is a compound according to claim 5.

15. A composition according to claim 10, wherein the active ingredient is N-(O-ethyl-S-n-propyl-thiono-thiolphosphoryl)-iso-butyramidine.

16. A composition according to claim 10, wherein the active ingredient is N-(O-ethyl-S-n-propyl-thiono-thiolphosphoryl)-acetamidine.

17. A composition according to claim 10, wherein the active ingredient is N-(O-ethyl-S-n-propyl-thiophosphoryl)-acetamidine.

18. A composition according to claim 10, wherein the active ingredient is O-ethyl-S-sec.butyl-cyclopropanecarbamidinothiophosphate.

19. A method of combating nematodes at a locus which comprises applying to the locus an effective amount of a compound according to claim 1.

20. A method according to claim 19, wherein the nematodes are plantpathogenic nemathodes.

* * * * *